United States Patent
Wang et al.

(10) Patent No.: US 9,439,729 B2
(45) Date of Patent: Sep. 13, 2016

(54) SYSTEM AND METHOD FOR MONITORING THERMAL ABLATION USING RADIOFREQUENCY ECHOES

(71) Applicant: Wisconsin Alumni Research Foundation, Madison, WI (US)

(72) Inventors: Peng Wang, Madison, WI (US); Christopher L. Brace, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/927,339

(22) Filed: Jun. 26, 2013

(65) Prior Publication Data
US 2015/0005757 A1    Jan. 1, 2015

(51) Int. Cl.
*A61B 18/10* (2006.01)
*A61B 18/18* (2006.01)
*A61B 18/00* (2006.01)

(52) U.S. Cl.
CPC .. *A61B 18/1815* (2013.01); *A61B 2018/00511* (2013.01); *A61B 2018/00529* (2013.01); *A61B 2018/00541* (2013.01); *A61B 2018/00577* (2013.01); *A61B 2018/00785* (2013.01); *A61B 2018/1869* (2013.01)

(58) Field of Classification Search
CPC ............ A61B 5/0507; A61B 18/1815; A61B 2018/1869; A61B 2018/00702; A61B 2018/00708; A61B 2018/00738; A61B 2018/00785; A61B 2018/00904
See application file for complete search history.

(56) References Cited

U.S. PATENT DOCUMENTS

| | | | | | |
|---|---|---|---|---|---|
| 4,344,440 | A | * | 8/1982 | Aaby et al. | 600/430 |
| 4,557,372 | A | * | 12/1985 | Rajagopal | 198/807 |
| 5,829,437 | A | * | 11/1998 | Bridges | 600/430 |
| 6,064,903 | A | * | 5/2000 | Riechers et al. | 600/407 |
| 7,101,369 | B2 | | 9/2006 | van der Welde | |
| 7,611,508 | B2 | | 11/2009 | Yang et al. | |
| 8,852,179 | B2 | * | 10/2014 | Ward et al. | 606/33 |
| 2010/0094271 | A1 | * | 4/2010 | Ward et al. | 606/33 |

OTHER PUBLICATIONS

Zhen Ji et al.; Expanded Modeling of Temperature-Dependent Dielectric Properties for Microwave Thermal Ablation; IOP Publishing; Phys. Med Biol. 56 (2011); pp. 5249-5264; UK.

Kazuyuki Saito et al.; Preliminary Study of Coagulation Monitoring by Antenna for Treatment during Microwave Coagulation Therapy; The Open Biomedical Engineering Journal, 2010, 4; pp. 13-15;JP.

Peng Wang et al.; Tumor Boundary Estimation Through Time-Domain Peaks Monitoring; Numerical Predictions and Experimental Results in Tissue-Mimicking Phantoms; IEEE Transactions on Biomedical Engineering, vol. 56, No. 11, Nov. 2009; pp. 2634-2641; US.

Peng Wang et al.; Tissue Dielectric Measurement Using an Interstitial Dipole Antenna; IEEE Transactions on Biomedical Engineering, vol. 59, No. 1, Jan. 2012; pp. 115-121; US.

* cited by examiner

*Primary Examiner* — Ronald Hupczey, Jr.
(74) *Attorney, Agent, or Firm* — Boyle Fredrickson, S.C.

(57) ABSTRACT

Radiofrequency energy emitted from and reflected back toward a thermal ablation probe may be used to detect a gradual dissolution of a reflective interface between a tumor and surrounding healthy tissue as the ablation zone passes through this interface providing a real-time guidance with respect to the progress of ablation.

15 Claims, 3 Drawing Sheets

SYSTEM AND METHOD FOR MONITORING THERMAL ABLATION USING RADIOFREQUENCY ECHOES

STATEMENT REGARDING FEDERALLY SPONSORED RESEARCH OR DEVELOPMENT

This invention was made with government support under CA142737 and CA149379 awarded by the National Institutes of Health. The government has certain rights in the invention.

CROSS REFERENCE TO RELATED APPLICATION

--

BACKGROUND OF INVENTION

The present invention relates to systems for thermal ablation of tumors and the like, for example, by microwave ablation, and in particular to a system for monitoring the progress of this ablation using radiofrequency signals.

Thermal ablation is a method of treating tumors, for example, in the liver, kidney or lung that serves as an alternative to surgical removal. In microwave thermal ablation, a slender microwave antenna is inserted through tissue to conduct microwave energy to a location of a tumor. The microwave energy absorbed by the tumor heats the tumor cells causing cell death.

Medical imaging including variants of conventional and contrast-enhanced ultrasound, computed tomography (CT) or magnetic resonance imaging (MRI) is used to confirm that the lesion fully covers both the original tumor and a margin of tissue surrounding that tumor. However, medical imaging can be expensive and may be negatively affected by bubbles or other changes during thermal ablation, and is therefore not routinely used intraprocedurally. Post-ablation imaging is not able to show treatment evolution or predict potential complications before they occur.

SUMMARY OF THE INVENTION

The present invention uses reflected radiofrequency signals transmitted from the ablation probe to monitor boundaries between the ablation zone, tumor and "background" surrounding healthy tissue. As the ablation progresses, the tumor-background boundary becomes indistinct signaling that the ablation has equalized the dielectric of the tumor and tissue outside of the tumor by the ablation crossing the tumor/healthy tissue boundary.

In one embodiment, the present invention provides an ablation apparatus having a probe adapted so that a distal end of the probe may be percutaneously inserted through tissue for thermal ablation of a tumor within the tissue. The apparatus further includes a transmitting circuit communicating with the probe when the latter is inserted into tissue to transmit a measurement radiofrequency signal from the distal end of the probe. A receiving circuit also communicates with the probe to receive an echo of the measurement radio frequency signal which includes the reflection caused by dielectric boundaries within the tissue and provides that signal to a processing circuit which analyzes the echo to extract echo signal from a dielectric boundary between the tumor and the tissue associated with thermal ablation of the tumor and to provide an output based on the extracted echo signal.

It is thus a feature of at least one embodiment of the invention to provide a technique for monitoring of thermal ablation suitable for real-time use that may deduce completion of ablation by monitoring dissolution of a reflective boundary between the tumor and healthy tissue and thus does not require accurate measurement of the often diffuse boundary of the ablation region itself.

The transmitting circuit may also transmit an ablation radio frequency signal from the distal end of the probe for thermal ablation of tissue at the distal end of the probe.

It is thus a feature of at least one embodiment of the invention to provide a monitoring system that is easily integrated with existing radiofrequency (including microwave) thermal ablation probes.

The transmitting circuit may alternate between an ablation radiofrequency signal and a measurement radiofrequency signal.

It is thus a feature of at least one embodiment of the invention to take advantage of the thermal inertia of tissue to interleave measurement into the ablation process with ablation to reduce interference between the two and yet provide near real-time monitoring.

The processing circuit may determine a distance of a source of the echo from the probe.

It is thus a feature of at least one embodiment of the invention to derive spatial information from the echo that may be used, in some embodiments, to isolate echo portions from the tumor boundary from the echo portions from the ablation boundary.

The determination of the distance may use at least one of time domain reflectometry and frequency domain reflectometry.

It is thus a feature of at least one embodiment of the invention to provide a system that may flexibly analyze radiofrequency signals to provide distance measurements. Generally frequency domain reflectometry may be implemented using a general-purpose ablation power supply.

The processing circuit may separate an echo portion associated with a dielectric boundary between the tumor and tissue from an echo portion associated with a dielectric boundary between ablated and unablated tissue.

It is thus a feature of at least one embodiment of the invention to remove the confounding influence of any echo from the ablation region itself.

The processing circuit may subtract from the echo an echo portion caused by a dielectric boundary between ablated and unablated tissue It is thus a feature of at least one embodiment of the invention to provide a simple method of reducing the undesired echo portions.

The echo portion caused by the ablation boundary may be determined by fitting of echo models to the echo data, the echo models based on echoes occurring in ablated tissue with no tumor.

It is thus a feature of at least one embodiment of the invention to facilitate generation of a wide range of echo models for different tumor-free echoes useful in a variety of ablation treatments.

The output from the processing circuit may provide a display indicating a strength of echo from the dielectric boundary between the tumor and tissue.

It is thus a feature of at least one embodiment of the invention to provide simple and intuitive real-time guidance of ablation progress to a physician or healthcare worker.

Alternatively or in addition the output may be used to control the thermal ablation applied to the tissue.

It is thus a feature of at least one embodiment of the invention to provide for automatic or semiautomatic ablation control.

The output may determine a time of continued ablation after the dielectric boundary between the tumor and tissue is substantially fully decreased.

It is thus a feature of at least one embodiment of the invention to provide improved guidance for termination of the ablation process.

These particular objects and advantages may apply to only some embodiments falling within the claims and thus do not define the scope of the invention.

DETAILED DESCRIPTION OF THE PREFERRED EMBODIMENT

Figure 1:
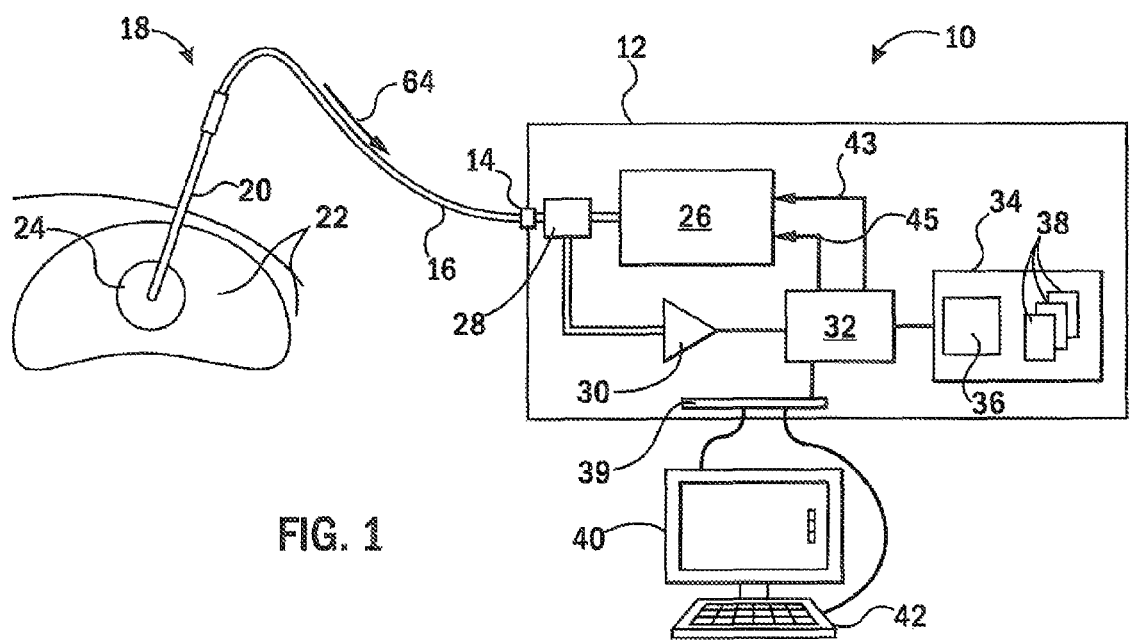
FIG. 1 is a block diagram of a thermal ablation system having a microwave power generator suitable for use with the present invention as connected to a microwave probe inserted through organ tissue into a tumor.

Referring now to FIG. 1, a microwave ablation system 10 may provide a microwave power generator 12 having an output connector 14 connecting via a flexible coaxial cable 16 to a microwave probe 18. The probe 18 provides a shaft 20 that may for example, be inserted percutaneously through healthy tissue 22 of an organ to position its distal end in a tumor 24. Microwave probes suitable for use with this invention are commercially available from a variety of sources and may be, for example, of the type described in U.S. Pat. No. 7,101,369, and 7,611,508 assigned to the assignee of the present invention and hereby incorporated by reference.

The microwave power generator 12 may include a frequency and power controllable microwave source 26 outputting microwave energy to a power splitter 28 positioned between the microwave source 26 and connector 14.

Generally, the microwave signals transmitted from the microwave source 26 through the splitter 28 first pass through the flexible coaxial cable 16 into the probe 18 and into the tumor 24 and surrounding tissue 22. Microwave energy reflected from the tumor 24 and surrounding tissue 22 then pass back into the flexible coaxial cable 16 and are directed by the splitter 28 to a receiving circuit 30 providing amplification and conversion of these echo signals into a digital signal that may be received by a computer 32.

The computer 32 may provide one or more processors communicating with a memory 34 holding a stored program 36 and data of models 38 whose operation and purpose will be described below. As will be generally understood in the art, the computer 32 may also provide a standard interface 39 communicating with a graphics display screen 40 and user input device 42 such as a keyboard or the like.

The computer 32 operating under the control of the stored program 36 provides a power output signal 43 and a frequency output signal 45 received by the frequency and power controllable microwave source 26 to control the frequency and power of the microwave signals output by the microwave source 26.

Figure 2:
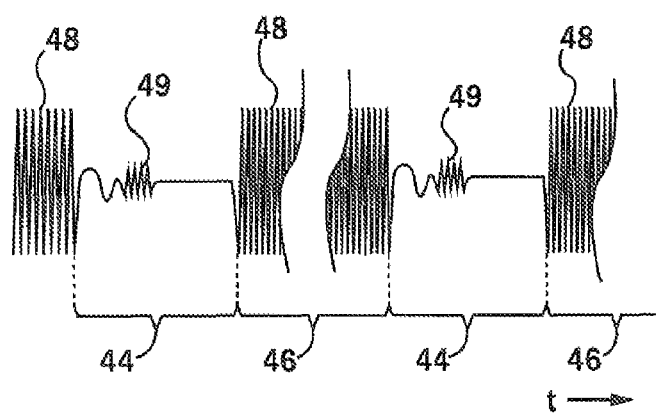
FIG. 2 is a fragmentary graph of microwave power transmitted from the microwave power supply of FIG. 1 versus time during interleaved treatment and measurement modes possible with the present invention.

Referring now also to FIG. 2, in particular, the computer 32 may control the frequency and power output by the microwave source 26 to switch between a first "measurement" mode 44 of relatively short duration, for example 5 seconds, and a second "ablation" mode 46 having a duration of as 30 seconds providing frequent measurements during the ablation.

During the measurement mode 44, low-power measurement microwave signals 49 are provided to the probe 18. These measurement microwave signals 49 are limited in power to a few milliwatts and the frequency is swept, for example, from 200 MHz to 10 GHz. The output of the splitter 28 to the receiving circuit 30 is active during this mode so that echo signals may be received.

During the ablation mode 46, high-power microwave signals 48 are provided to the probe 18. These high-power microwave signals 48 are coupled into the tumor 24 to heat and ablate the tumor tissue. Generally the high-power microwave signals will be at a constant frequency in a frequency range of about 915 MHz to 2.50 GHz although other frequencies are possible. Power levels of 10 to 200 Watts or more may be output during this ablation mode. The output of the splitter 28 to the receiving circuit 30 may be a disabled or shunted during this mode.

Figure 3:
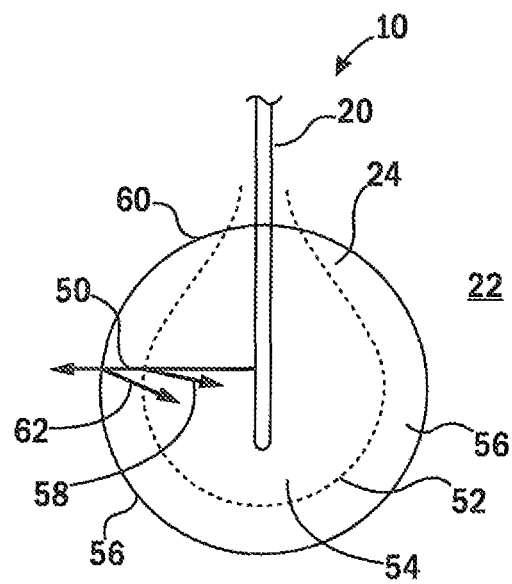
FIG. 3 is an expanded cross-sectional view of the tumor of FIG. 1 and inserted probe showing a first interface between the tumor and surrounding healthy tissue and a second interface between ablated tissue and outside, unablated tissue, both of which provide boundaries.
Figure 5:
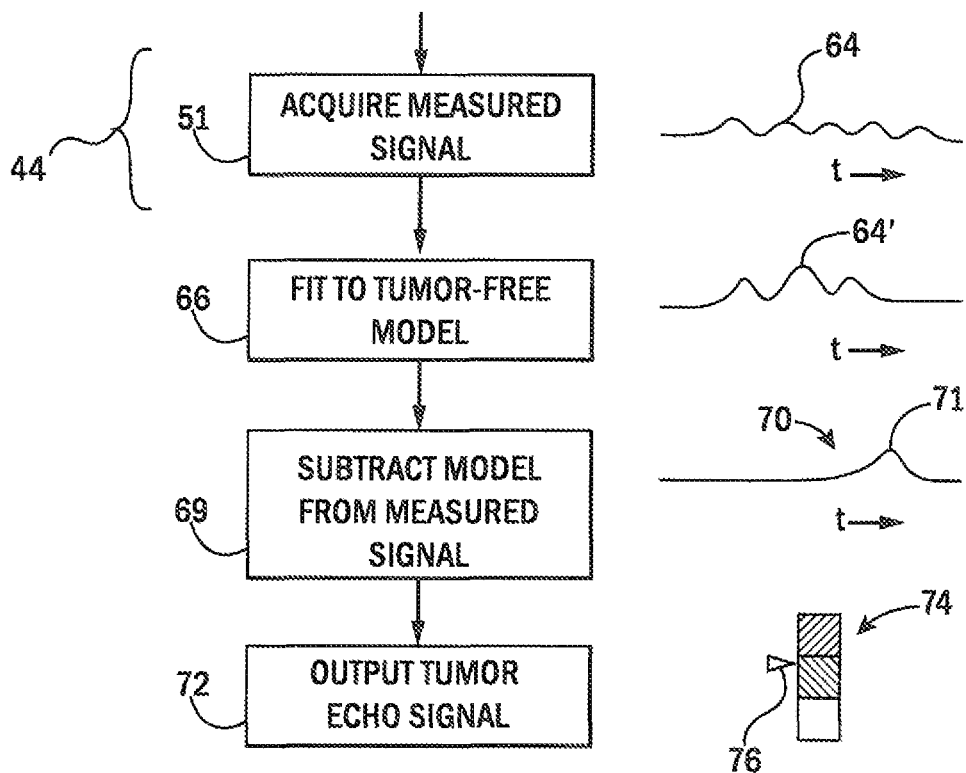
FIG. 5 is a flowchart of a program executed by the microwave power supply of FIG. 1 showing the principal steps of signal processing provided by that microwave power generator.

Referring now to FIGS. 2, 3 and 5, during the measurement mode 44, as indicated by process block 51, measurement microwave signals 49 generated by the microwave source 26 will be transmitted from the distal end of the shaft 20 of the probe 18 outward as indicated by arrow 50. During this transmission, the energy of the measurement microwave signal 49 will pass through an ablation boundary 52 between ablated region 54 of tissue closest to the shaft 20 and an unablated region 56 outside of the ablated region 54. The dielectric constant of these two regions 54 and 56 will generally differ significantly, albeit over a diffuse boundary, causing a time-extended ablation interface reflection 58. The energy of the measurement microwave signal 49 output by the microwave source 26 will also cross through a tumor boundary 60 between the tumor 24 and healthy tissue 22 surrounding the tumor 24. Again a difference in dielectric constant between these two regions will cause a tumor interface reflection 62 directing energy back toward the probe 18. This tumor interface reflection 62 may be sharper, that is shorter in time, than the ablation interface reflection 58.

The energy of this ablation interface reflection 58 and tumor interface reflection 62 pass back through the probe 18 to be received by splitter 28 and directed to the receiving circuit 30 (shown in FIG. 1) as a measured echo 64 that may be stored by the computer 32 in memory 34 as a series of amplitude values associated with different sample times. Generally, the combination of ablation interface reflection 58 and tumor interface reflection 62 from both the ablation boundary 52 and tumor boundary 60 make it difficult to discern the echo from the tumor boundary 60 in the measured echo 64.

In one embodiment, the measured echo 64 may be measured in the time-domain using the techniques of time-domain reflectometry in which a short pulse (not shown) is transmitted by the microwave source 26 and its echo recorded with a high-speed analog to digital converter.

Preferably, however, as depicted in the embodiment of FIG. 2, measured echo 64 is extracted from the frequency-swept measurement microwave signal 49 by using the techniques of frequency domain reflectometry in which an inverse Fourier transform of a the frequency-swept measurement microwave signal 49 is used to extract a time domain measured echo 64. This technique may better work with existing ablation radiofrequency power sources that can be swept in frequency and may eliminate the need for additional gating circuitry.

Figure 4:
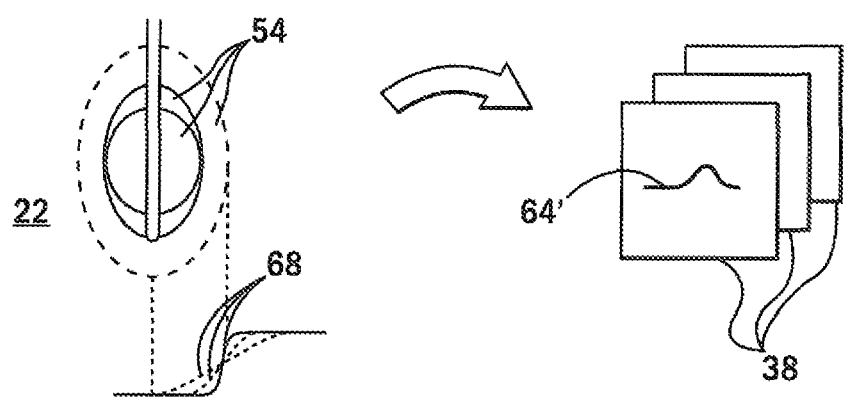
FIG. 4 is a process diagram depicting steps in the generation of reflection data for tumor-free tissue using a modeling process.

Referring now to FIG. 4, generally the tumor interface reflection 62 may be extracted from the ablation interface reflection 58 by de-emphasizing the latter based on the spatial information encoded into the time dimension of the echo. In one embodiment, the invention develops a set of models 38 from a computer simulation, each, model 38 representing a simulation of echo signals, termed a modeled, tumor-free echo 64', that might occur in healthy tissue 22 in the absence of a tumor 24. In this respect, the tumor-free echo 64 simulates only the ablation interface reflection 58 and not the tumor interface reflection 62.

In particular, a set of tumor-free models 38 is developed simulating ablation zones in different tissue types, for example simulating liver, kidney, and lung or others common tissues. The set of tumor-free models 38 also provides simulations of different ablation zone sizes and shapes (for example, varying, from circular to oval and varying as to principal diameter). In addition, the set of tumor-free models 38 also provides for a different dielectric transition gradient 68 between the ablated region 54 and the surrounding tissue 22. Each of these different tumor-free models 38 having variations of size, shape, transition gradient, and tissue type, results in a tumor-free echo 64'.

Referring again to FIG. 5, as indicated by process block 66, the user may identify a tissue type currently undergoing ablation and the program 36 may identify only the tumor-free models 38 related to that tissue type to provide a subset of models 38. The tumor-free echo 64' of the subset of models 38 is then compared to a given measured echo 64 to find a closest match, for example, by a correlation process. The correlation will not be perfect because measured echo 64 includes not only ablation interface reflection 58 as modeled but also tumor interface reflection 62 as not modeled. This correlation process may be repeated over time for each newly measured echo 64. The best correlation criteria for matching a tumor-free echo 64 to a measured echo 64 may also give weighting to matches that preserve general continuity between the model's diameters, shapes and gradients over time.

At process block 69, the best matching tumor-free echo 64' is then subtracted from the measured echo 64 to extract a tumor boundary signal 70 (being close to ablation interface reflection 58) having a peak 71 whose amplitude is primarily determined by the degree of dielectric difference between the tumor 24 and healthy tissue 22 and its transition gradient.

Generally as the ablation boundary 52 crosses the tumor boundary 60, the distinctiveness of the peak 71 in isolated tumor boundary signal 70 will diminish indicating a degree of completion of the ablation process.

At process block 72, an output may be provided, for example on display screen 40, displaying or representing the height or area of this peak 71. This representation may be continuous in nature and represented numerically or with a biographical symbol, or may compare the height or area of peak 71 to a threshold to provide a simple binary output. In one example depicted to the right of process block 72, an output 74 may provide colored zones of a scale and an indicator arrow 76 or the like indicating a position on the scale indicating a relative degree of completion of the ablation process.

Figure 6:
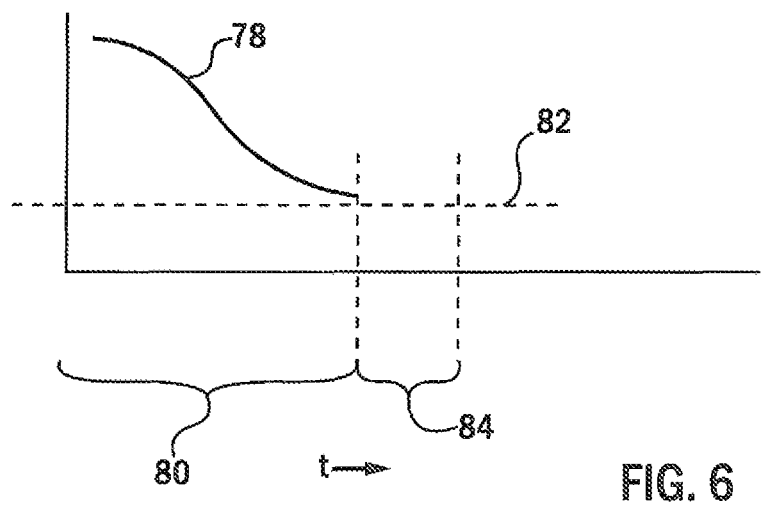
FIG. 6 is a graph of reflected energy at the tumor/tissue boundary with respect to time as it becomes indistinct showing use of that information in controlling a duration of the ablation.

Referring now to FIG. 6, the ability to track the reflection at the tumor boundary 60 as it diminishes over time allows a time profile 78 to be developed indicating generally the change in the peak 71 (shown in FIG. 5) providing additional longitudinal information. Time profile 78, for example, may allow determination of an interval 80 measuring the time during which the time profile 78 is above a predetermined threshold 82 representing, for example, a predetermined percentage of an asymptotic limit to the decrease in the time profile 78 or another empirically derived threshold. The length of this interval 80, which generally indicates the time it takes for the ablation boundary 52 to pass through the entirety of the tumor 24 and across the tumor boundary 60 may be used to judge an additional ablation time 84 providing an adequate margin around the tumor 24 or to otherwise automatically control the power of microwave source 26, for example, reducing the power after the ablation boundary 52 crosses the tumor boundary 60 to provide a temperature maintenance mode to ensure tumor cell death without further outward progress of the ablation boundary 52.

While the present invention is particularly well-suited to microwave ablation, it will be appreciated that it can be used for lower frequency ablation, for example, by combining a standard radiofrequency ablation probe with a microwave antenna and even for other types of thermal ablation including cryoablation by a similar strategy in which the necessary antenna is attached to the cryoablation probe. The described combined function of the microwave source 26 in producing both a measurement microwave signal 49 and a high-power microwave signal 48 may be split into multiple devices.

The term radiofrequency as used herein is intended to include generally both microwave and radio frequencies having a longer wavelength than microwave frequencies unless context would otherwise require.

It will be appreciated that the ability to deduce approximate distance measures of the reflective interface generating echoes in the present invention allows additional or alternative signal processing to be extract the tumor interface reflection 62 from the tumor/healthy tissue boundary including the establishment of a priori or empirically established spatial windows for truncating or weighting the data or the like such as may move outward over time at a predetermined rate. The term "dielectric boundary" as used herein means a boundary established with regions having different dielectric constants that would cause a reflection of transiting radio energy.

While the present invention has been discussed for use with radiofrequency ablation, it will be appreciated that it may be used to detect the progress of other types of tissue disruption usable to kill tumor cells including cryoablation, laser ablation, irreversible electroporation, and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer system" can be understood to include one or more processors or cores that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An ablation apparatus comprising:
a probe adapted for percutaneous insertion of a distal end of the probe through tissue for disruption of a tumor within the tissue;
a transmitting circuit adapted to communicate with the probe when the latter is inserted into tissue to transmit a measurement radiofrequency signal from the distal end of the probe;
a receiving circuit adapted to communicate with the probe to receive an echo of the measurement radio frequency signal caused by dielectric boundaries; and
a processing circuit including an electronic computer configured to execute a program stored in a non-transient medium and configured to operate to process the echo during ablative procedure to track a boundary of the disruption by
   (i) using the echo to develop a tumor-free echo modeling the tissue under ablation to provide an ablation boundary echo but not an echo from a tumor-healthy tissue boundary,
   (ii) subtracting the tumor-free echo from the echo to provide a tumor-healthy tissue echo, and
   (iii) using the tumor-healthy tissue echo to provide an output indicating passage of an ablation boundary past a tumor-healthy tissue boundary.

2. The ablation apparatus of claim 1 wherein the transmitting circuit is adapted to also transmit an ablation radio frequency signal from the distal end of the probe for thermal ablation of tissue at the distal end of the probe.

3. The ablation apparatus of claim 2 wherein the transmitting circuit is adapted to alternate between an ablation radiofrequency signal and a measurement radiofrequency signal.

4. The ablation apparatus of claim 1 wherein the processing circuit is configured to further operate to determine distance of a source of the echo from the probe.

5. The ablation apparatus of claim 4 wherein the determination of distance uses at least one of time domain reflectometry and frequency domain reflectometry.

6. The ablation apparatus of claim 1 wherein the tumor-free echo is determined by fitting of echo models to the echo data, the echo models based on echoes in ablated tissue in the absence of a tumor.

7. The ablation apparatus of claim 1 wherein the output from the processing circuit is further configured to operate to provide a display indicating a change in the strength of echo from the dielectric boundary between the tumor and tissue.

8. The ablation apparatus of claim 1 wherein the output is adapted to control the thermal ablation applied to the tissue.

9. The ablation apparatus of claim 8 wherein the output is adapted to determine a time of continued ablation after the dielectric boundary between the tumor and tissue is fully decreased.

10. The ablation apparatus of claim 1 wherein the transmitting circuit is a microwave transmitter.

11. The ablation apparatus of claim 1 wherein the probe is a microwave antenna.

12. A monitoring system for in vivo tumor disruption comprising:
a microwave transmitter adapted to connect to an antenna for percutaneous insertion into a tumor within tissue, the microwave power source adapted to provide a low power microwave output that sweeps through a frequency range below a power level providing thermal ablation;
a microwave receiver adapted to receive reflected power of the low power microwave output into the antenna; and
an electronic computer configured to execute a program stored in a non-transient medium to communicate with the microwave receiver and to analyze the reflected power during ablative procedure to develop a tumor-free reflected power associated with the tissue under ablation absent a tumor-healthy tissue boundary and subtract the tumor-free reflected power from the reflected power to provide an output indicating a decrease in reflected power associated with the boundary between the tumor and tissue indicating progress of the tumor disruption process.

13. The monitoring system of claim 12 wherein the microwave power source further provides a high-power radiofrequency output for ablation of the tumor through radiofrequency energy coupled to the tumor out of the antenna.

14. The monitoring system of claim 12 wherein the microwave transmitter provides a port adapted to communicate with a tissue disrupting power source to provide interleaved periods of application of tissue disrupting power to the tumor and to receive reflected power.

15. A method of performing thermal ablation using an ablation apparatus having:
   a probe adapted for percutaneous insertion of a distal end of the probe through tissue for disruption of a tumor within the tissue;
   a transmitting circuit adapted to communicate with the probe when the latter is inserted into tissue to transmit a measurement radiofrequency signal from the distal end of the probe;
   a receiving circuit adapted to communicate with the probe to receive an echo of the measurement radio frequency signal caused by dielectric boundaries; and
   a processing circuit including an electronic computer configured to execute a program stored in non-transient medium and configured to operate to process the echo during thermal ablation to track a boundary of the disruption by (i) using the echo to develop a tumor-free echo modeling the tissue under ablation to provide an ablation boundary echo but not an echo from a tumor-healthy tissue boundary, (ii) subtracting the tumor-free echo from the echo to provide a tumor-healthy tissue echo, and (iii) using the tumor-healthy tissue echo to provide an output indicating passage of an ablation boundary past a tumor-healthy tissue boundary;

the method comprising the steps of:
inserting a probe percutaneously into tissue so that a distal end of the probe is received within a tumor within the tissue;
treating the tumor using the probe;
contemporaneously with the treatment, transmitting a measurement radiofrequency signal from the distal end of the probe;
analyzing a received echo of the measurement radio frequency signal caused by dielectric boundaries within the tissue; and
outputting an indication of a decrease in a dielectric boundary between the tumor and the tissue associated with thermal ablation of the tumor based on the analyzing of the received echo.

* * * * *